US012569425B2

(12) United States Patent
Allen et al.

(10) Patent No.: US 12,569,425 B2
(45) Date of Patent: Mar. 10, 2026

(54) AEROSOL HAIR CARE PRODUCT

(71) Applicant: Conopco, Inc., Englewood Cliffs, NJ (US)

(72) Inventors: Elizabeth Sara Allen, Derbyshire (GB); Gillian Brown, Heswall (GB); Robert Wayne Dawson, Wirral (GB); Leslie Joseph Luke Joinson, Prenton (GB)

(73) Assignee: Conopco, Inc., Englewood Cliffs, NJ (US)

( * ) Notice: Subject to any disclaimer, the term of this patent is extended or adjusted under 35 U.S.C. 154(b) by 459 days.

(21) Appl. No.: 18/015,440

(22) PCT Filed: Jul. 15, 2021

(86) PCT No.: PCT/EP2021/069777
§ 371 (c)(1),
(2) Date: Jan. 10, 2023

(87) PCT Pub. No.: WO2022/013362
PCT Pub. Date: Jan. 20, 2022

(65) Prior Publication Data
US 2023/0270656 A1 Aug. 31, 2023

(30) Foreign Application Priority Data
Jul. 17, 2020 (EP) ..................................... 20186514

(51) Int. Cl.
| | |
|---|---|
| *A61K 8/73* | (2006.01) |
| *A61K 8/04* | (2006.01) |
| *A61K 8/30* | (2006.01) |
| *A61Q 5/02* | (2006.01) |
| *B65D 83/48* | (2006.01) |

(52) U.S. Cl.
CPC .............. *A61K 8/732* (2013.01); *A61K 8/046* (2013.01); *A61K 8/30* (2013.01); *A61Q 5/02* (2013.01); *B65D 83/48* (2013.01); *A61K 2800/31* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 1,084,203 A | 1/1914 | Ellis |
| 6,581,807 B1 | 6/2003 | Mekata |
| 8,191,739 B1 | 6/2012 | Cash et al. |
| 2008/0253973 A1 | 10/2008 | Tamarkin et al. |
| 2009/0104138 A1 | 4/2009 | Shimatani et al. |
| 2010/0269844 A1 | 10/2010 | Gawtrey et al. |
| 2012/0031419 A1 | 2/2012 | Batt et al. |
| 2012/0034173 A1 | 2/2012 | Batt et al. |
| 2016/0100667 A1 * | 4/2016 | Aubert et al. |
| 2019/0256278 A1 | 8/2019 | Brown et al. |
| 2020/0016044 A1 | 1/2020 | Rodrigues et al. |
| 2020/0146950 A1 | 5/2020 | Brown et al. |
| 2020/0148459 A1 | 5/2020 | Bartolucci et al. |

FOREIGN PATENT DOCUMENTS

| | | | |
|---|---|---|---|
| CN | 103002860 | | 3/2013 |
| CN | 109843384 | | 6/2019 |
| EP | 0753561 | | 1/1997 |
| EP | 2407145 | | 1/2012 |
| EP | 2407145 A1 * | | 1/2012 |
| EP | 2570110 | | 3/2013 |
| GB | 2270698 | | 3/1994 |
| WO | 9401511 | | 1/1994 |
| WO | 2009039565 | | 4/2009 |
| WO | 2017076836 | | 5/2017 |
| WO | 2018073070 | | 4/2018 |
| WO | WO2018073070 A1 * | | 4/2018 |
| WO | 2018162701 | | 9/2018 |

OTHER PUBLICATIONS

Extended European Search Report on European Patent Application No. EP20186526.8 dated Jan. 28, 2021.
Extended European Search Report on European Patent Application No. 20186514.4 dated Dec. 17, 2020.
Nasr et al., "Next Generation of Consumer Aerosol Valve Design Using Inert Gases", Journal of Mechanical Engineering Science, Proceedings of the Institution of Mechanical Engineers, Part C., (2015), vol. 229(16), pp. 2952-2976.
International Search Report and Written Opinion on International Patent Application No. PCT/EP2021/069777 dated Oct. 18, 2021.
International Search Report and Written Opinion on International Patent Application No. PCT/EP2021/068168 dated Sep. 27, 2021.
International Preliminary Report on Patentability on International Patent Application No. PCT/EP2021/068168 dated Jul. 17, 2020.

* cited by examiner

*Primary Examiner* — Robert A Wax
*Assistant Examiner* — Kimberly Barber
(74) *Attorney, Agent, or Firm* — Carter, DeLuca & Farrell, LLP; George Likourezos; Bret P. Shapiro

(57) ABSTRACT

An aerosol hair care product includes a pressurisable container a propellant, a hair care formulation, and a spraying device. The pressurisable container is at a pressure of $9\times10^5$ to $11\times10^5$ Pa. The pressurisable container includes a container wall which encloses a reservoir. The propellant is contained within the reservoir. The propellant includes an insoluble compressed gas and has a first weight. The hair care formulation is contained within the reservoir. The hair care formulation has a second weight and includes starch having a third weight. The third weight is 3 to 15% of a sum of the first weight and the second weight. The spraying device is attached to the pressurisable container. The spraying device is configured to facilitate dispensing of the hair care formulation from the reservoir. The spraying device includes an actuator and a valve.

20 Claims, 2 Drawing Sheets

AEROSOL HAIR CARE PRODUCT

CROSS-REFERENCE TO RELATED APPLICATIONS

This application claims priority to International Patent Application No. PCT/EP2021/069777, filed on Jul. 15, 2021, and European Patent Application No. 20186514.4, filed on Jul. 17, 2020, both of which are incorporated herein by reference in their entireties.

FIELD OF THE INVENTION

The present invention relates to an aerosol hair care product having reduced volatile organic compound (VOC) content.

BACKGROUND OF THE INVENTION

Aerosol products have been popular since their inception, because of their marked ease of use and variety of applications. The term "aerosol" includes products that can be dispensed in a stream, spray, powder, gel or a foam. Innovations in this area of technology have enabled aerosol products that contain organic solvents or water or combinations thereof, as well as products that foam upon ejection and products that delay foaming after ejection.

Typical aerosol hair care products comprise a pressure-resistant container, a nozzle, a propellant, and a hair care formulation. A hairspray composition is normally ejected from such products via aerosol-forming nozzle. See, for example, US2009/0104138AI.

Typically, two types of propellants are used in aerosol products: liquefied gases and compressed gases.

The use of a compressed gas alone as a propellant has drawbacks, in certain applications, where the pressure is not sustained over the use of the aerosol container; the contents are over-pressurized at the beginning of the consumer's use and become under-pressurized prior to the complete use of the product. The amount of compressed gas retained in a product is dependent on its solubility in the product being dispensed. The less soluble the compressed gas is in the product, the more compressed gas is retained in the vapor phase (i.e., the headspace) within the aerosol container. Thus, internal vapour pressure of the aerosol dispenser diminishes as the contents are depleted, causing changes in the rate and characteristics of the spray. In particular, the use of nitrogen as a compressed gas propellant has been discouraged in the art because of nitrogen's insolubility in the product; this insolubility causes rapid pressure depletion and changed spray characteristics, and for these reasons nitrogen generally has limited applications as a compressed gas propellant in the aerosol industry.

The addition of LPGs and/or HFCs contributes to the aerosol product's desirable spray characteristics. More specifically, certain types of liquefied gases allow the product to foam upon dispensing. However, the use of LPGs or HFCs alone in typical formulations known in the art has its own drawbacks concerning cost and environmental profile, as discussed below. Despite these drawbacks, liquefied gases are presently used as propellants in many aerosol products because of the desirability of foaming aerosol products. In order to foam upon dispensing, aerosol products must contain liquefied gas; for this reason, liquefied gas—whether LPGs, HFCs, and blends thereof—is used in the aerosol industry as the propellant in a variety of foaming aerosol products.

As mentioned above, certain concerns influence the use of LPGs. First, the use of LPGs has significant environmental concerns, as LPGs fall within a class of chemicals known as volatile organic compounds ("VOCs"). VOCs are precursors of ground level smog, which is a significant daily environmental hazard in many urbanized areas. On an individual level, VOCs have been associated with a variety of health problems, ranging from irritation to chronic problems.

Environmental sustainability has become a matter of growing interest in aerosol applications. The environment is benefited by a product that, compared to conventional aerosols, emits less propellant (e.g., volatile organic compound (VOC).

For the above reasons, there is a desire to use as little liquefied gas as possible.

The spraying device attached to the container of the aerosol product typically comprises a valve with a specific vapour phase tap (VPT) and a restricted tail piece (RTP) to enable sufficient breakup of droplets and minimize the risk of blockage. However, the use of a VPT in compressed gas/nitrogen containing products is disadvantageous. Due to the insolubility of the compressed gas/nitrogen in the liquid product, there will not be rebalance of the pressure in the headspace of the container and as such the inclusion of a VPT will give accelerated release of the compressed gas/nitrogen to result in inconsistent product performance, poor longevity and residual liquid product in the container. Whilst restriction of the RTP would typically result in an increased blockage risk.

There remains a need for an aerosol product with compressed gas as the propellant while maintaining product performance, longevity and/or minimizing residual product.

It is therefore an object of the present invention to provide an aerosol product with compressed gas (e.g. nitrogen) as the propellant while maintaining product performance, longevity and/or minimizing residual product.

It is another object of the present invention to provide an aerosol dry shampoo product with compressed gas as the propellant which has a product performance similar to or better than an aerosol dry shampoo product with liquefied gas as the propellant.

It is yet another object of the present invention to provide an aerosol product with reduced VOC content.

Surprisingly, it has been found that product performance of an aerosol product using compressed gas as the propellant can be maintained by a specific valve configuration to control the spray rate, in combination with the pressure in the container.

SUMMARY OF THE INVENTION

Accordingly, in a first aspect, the present invention provides an aerosol hair care product, which comprises: a pressurisable container comprising a container wall which encloses a reservoir for storing a hair care formulation, and a propellant; a hair care formulation comprising from 3 to 15% starch, by total weight of the combined hair care formulation and propellant; a spraying device attached to the container for dispensing the hair care formulation from the reservoir of the container, which comprises a valve and an actuator, wherein the valve comprises a valve body, said valve body comprising a stem and a spring means; and wherein the valve comprises a restricted tail piece (RTP) of diameter 0.50 mm to 0.55 mm, and a vapour phase tap (VPT) of diameter 0.30 to 0.34 mm; and wherein the propellant is an insoluble compressed gas and the pressure in the container is from $9\times10^5$ to $11\times10^5$ Pa (9 to 11 bar).

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

BRIEF DESCRIPTION OF THE FIGURES

Embodiments of the invention will now be described with reference to the following non-limiting drawings in which:

FIG. 1 is a side view of a hairspray product comprising a pressurisable container (1) having a container wall (2) and a reservoir (3); with a spraying device (4) comprising an actuator (5) having an insert (6) with an exit orifice (7).

FIG. 2 is a cross section view of a spraying device (4) comprising an actuator (5) having a main spray channel (8) and an insert (6) with an exit orifice (7). A stem socket is also shown.

FIG. 3 is a cross sectional view of a valve (10) used in the hairspray product of the invention, where the valve is installed in the container, seated in a valve cup (16). The valve (10) comprises a valve body (11), said valve body comprising a stem (12) and a spring means (13); and wherein the valve has a restricted tail piece (RTP) (14) with a diameter indicated by a double ended arrow "A", and a vapour phase tap (VPT) (15). The valve cup (16) comprises an outer gasket (17) and an inner gasket (18).

DETAILED DESCRIPTION OF THE INVENTION

Figure 1:
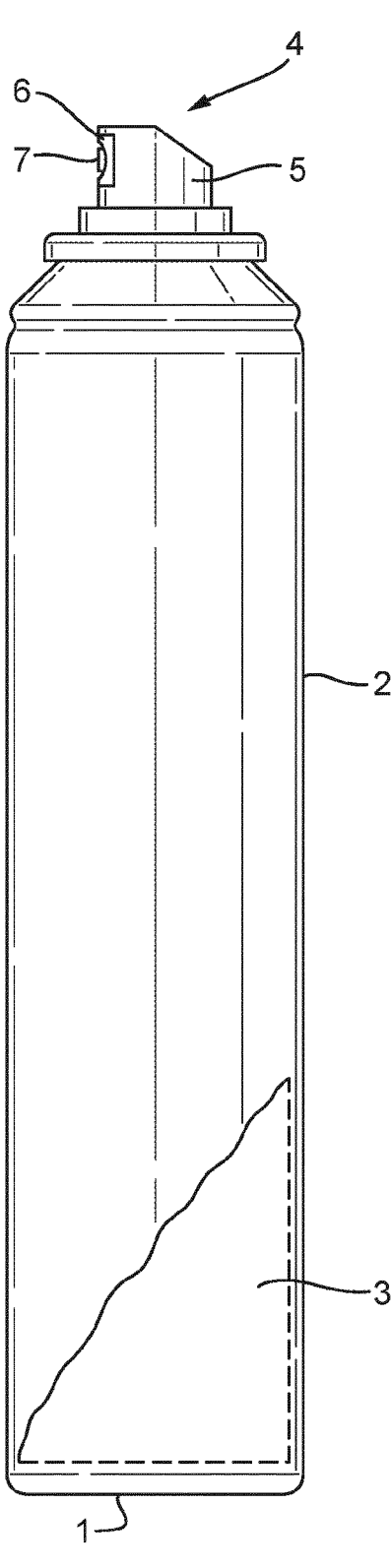
FIG. 1 is a side view of a hair care product in accordance with the invention.
Figures 2, 3:
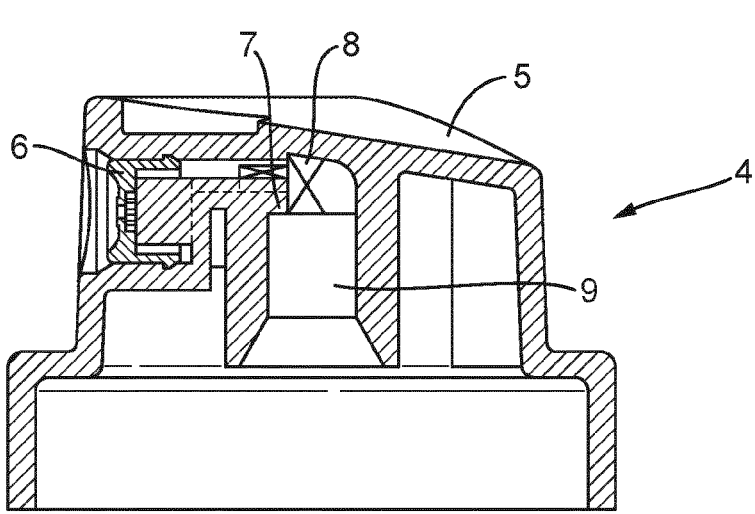
FIG. 2 is a cross section view of a spraying device (4) used in the hairspray product of the invention.
FIG. 3 is a cross section view of a valve (5) used in the hairspray product of the invention, where the valve is installed in the container (seated in a valve cup (16)).

The product relates to an aerosol hair care product comprising: a container comprising a reservoir for a hair care formulation and a compressed gas propellant, and a spraying device attached to the container.

The product comprises from 85% to 95% hair care formulation, preferably at least 86%, more preferably at least 87%, still more preferably at least 89% but typically not more than 93%, more preferably not more than 92% or still more preferably not more than 91% or even 90%, by total weight of the combined hair care formulation and propellant.

Typically, a container is filled to 5 to 25%, more preferably 8 to 20%, still more preferably 10 to 15% by volume of the hair care formulation and then pressurised to the fill pressure according to the invention with the inert propellant.

The product comprises from 7% to 14% propellant, preferably at least 8%, more preferably at least 9%, still more preferably at least 10% but typically not more than 13%, preferably not more than 12% or even 11% by total weight of the combined hair care formulation and propellant.

Conventional spray rates are typically in the range of from 0.5 to 1.5 g/sec. The product of the invention delivers 80 to 20% of this range, preferably 70 to 30%, most preferably from 60 to 40% of this spray rate.

The Pressurisable Container

The pressurisable container comprises a container wall which encloses a reservoir for storing a hair care formulation, and a propellant.

The container wall may be predominantly straight, curved or tapered.

The container preferably has a volume (so-called over fill capacity) of from 300 to 350 ml, more preferably from 310 to 340 ml, most preferably from 320 to 330 ml.

In one embodiment, the container with a volume of 330 ml has a base (hair care formulation) fill level of 92.4% by total weight of the combined hair care formulation and propellant.

The container preferably has a diameter of from 35 to 70 mm, more preferably from 45 to 60 mm.

The Propellant

The propellant according to the invention are preferably compressed gasses. Suitable compressed gases should be inert and insoluble. In a preferred embodiment, nitrogen is the compressed gas, because nitrogen is inert and is not soluble in water. Other inert, insoluble compressed gases include helium and argon; both of these gases would be expected to work effectively as compressed gas propellants. Compared to nitrogen, helium and argon present practical drawbacks because they are more expensive and impractical than nitrogen for use in aerosol products. However, from a scientific standpoint, helium and argon would be expected to be acceptable propellants, due to their inert nature and insolubility. Compared to argon, helium would be a better substitute for nitrogen, although helium's low molecular weight may cause significant leakage problems in an aerosol container. In the aerosol industry, carbon dioxide and nitrous oxide have also been used as compressed gases to act as propellants. However, nitrous oxide and carbon dioxide are soluble in water and a variety of organic solvents, and to the extent the compressed gas is soluble, the vapor pressure of the compressed gas will be depressed due to its solubility in the aerosol formula concentrate. Hence, insoluble compressed gasses are used in the present invention with nitrogen being the most preferred.

The compressed gas is added to the container in an amount sufficient to provide an absolute pressure of $9\times10^5$ to $11\times10^5$ Pa (9 to 11 bar), preferably $10\times10^5$ to $11\times10^5$ Pa (10 to 11 bar), most preferably $10.7\times10^5$ Pa (10.7 bar).

In one of the embodiments, the propellant is an insoluble compressed gas mixed with one or more liquefied gasses. One or more liquefied gases are included to the compressed gas preferably at levels of 3 to 16%, more preferably 5 to 15% by weight of the hair care formulation.

It is found that inclusion of one or more liquefied gasses to the compressed gas counteracts the pressure drop observed towards the end of the can lifetime. When filling with the propellant, after adding the hare care formulation, the container is first filled with 2 to 10 g of liquefied gas followed by the compressed gas to reach a pressure of $9 \times 10^5$ to $11 \times 10^5$ Pa (9 to 11 bar), preferably $10 \times 10^5$ to $11 \times 10^5$ Pa (10 to 11 bar), most preferably $10.7 \times 10^5$ Pa (10.7 bar).

Liquefied gases that are used as propellants can include liquefied petroleum gases ("LPGs") and hydrofluorocarbons ("HFCs"). As used in the context of this patent, the term "liquefied gas" is used to encompass both LPGs and HFCs. In the aerosol industry, LPGs include hydrocarbon propellants (e.g., propane, n-butane, isobutane). In the aerosol industry, HFCs include 1,1 difluoroethane (CH3CHF2), known in the aerosol industry as "152a," and 1,1,1,2 tetrafluoroethane (CF3CH2F), known in the aerosol industry as "134a."

Three LPGs are preferred: n-butane, isobutane, and propane. These LPGs fall into a class also often referred to as "hydrocarbon propellants." N-butane (C4H10(n)) is commonly referred to as "A-17" in the aerosol industry, as it has a 70° F. (21° C.) vapor pressure of 17 psig (1.17 bar(g), $1.17 \times 10^5$ Pa(g)). Isobutane (C4H10(iso)) is commonly referred to as "A-31" in the aerosol industry, as it has a 70° F. (21° C.) vapor pressure of 31 psig (2.14 bar(g), $2.14 \times 10^5$ Pa(g)). Propane (C3H8) is commonly referred to as "A-108" in the aerosol industry, as it has a 70° F. (21° C.) vapor pressure of 108 psig (7.45 bar(g), $7.45 \times 10^5$ Pa(g)). Most preferred LPG is a blend of n-butane, isobutane, and propane, which is also the most preferred liquefied gas.

In addition to n-butane, isobutane, and propane, other hydrocarbon propellants may also be used. For example, isopentane and n-pentane may also behave in the same manner as n-butane, isobutane, and propane.

The Hair Care Formulation

The product comprises a hair care formulation, which is preferably a dry shampoo composition comprising starch and a conditioning agent in an alcoholic composition. It is well known in the art that a water-based composition leads to consumer negative performance such as curl droop, long drying times and stickiness on the hair. These negatives are not experienced with alcoholic compositions.

The starch according to the invention includes starch derivates. Preferably the starch is selected from corn starch, tapioca starch, rice starch, and modified starch in particular, modified corn starch and tapioca starch. A preferred modified starch is aluminum starch octenyl succinate.

The starch is present in a concentration of 3 to 15%, preferably at least 6%, more preferably at least 7%, still more preferably at least 8%, even more preferably at least 9%, but typically not more than 14%, preferably not more than 13%, more preferably not more than 12%, still more preferably not more than 11%, even more preferably not more than 10% or even 9% by total weight of the combined hair care formulation and propellant.

Isopropyl myristate may be used in the present invention as a preferable conditioning agent.

The isopropyl myristate is optionally present in a concentration of 0.5 to 4%, preferably at least 0.75%, more preferably at least 1%, still more preferably at least 1.25%, even more preferably at least 1.5%, but typically not more than 3.5%, preferably not more than 3%, more preferably not more than 2.5%, still more preferably not more than 2%, by total weight of the combined hair care formulation and propellant.

Preferably, the hair care formulation of the present invention comprises an anti-caking agent which is preferably silica. Preferably, the anti-caking agent is present in the base from 0.1 to 1% by total weight of the combined hair care formulation and propellant.

Preferably, the hair care formulation of the present invention comprises an alcohol. The alcohol is preferably selected from ethanol, isopropyl alcohol, butanol, most preferably ethanol.

The alcohol is optionally present in an amount of from 50 to 90 wt % by total weight of the combined hair care formulation and propellant, preferably at least 60 wt %, more preferably at least 65%, still more preferably at least 70%, even more preferably at least 75% but typically not more than 85%, more preferably 80% by total weight of the combined hair care formulation and propellant.

Further optional ingredients present in the base may include propylene glycol, fragrance, emotives.

The Spraying Device

Attached to the container is a spraying device for spraying the hair care formulation onto a substrate, which comprises a valve and an actuator.

Without wishing to be bound by a theory, it is thought that the use of an inert gas increases the risk of blockage of the valve, because compressed inert gas is not soluble in the liquid product. While soluble (liquified) gasses cause rebalancing of the pressure in the headspace by evaporation, inert pressurised gasses cannot, and by using a standard vapour phase tap (VPT), this is thought to cause accelerated release of inert compressed gas and consequently inconsistent product performance, poor longevity and residual liquid product remaining in the spray can. Restriction of the restrictive tail piece (RTP) would typically result in an increased blockage risk of a dry shampoo.

The specific configuration of the valve of the present invention provides a parity performing dry shampoo, having a comparable breakup and minimal blockage, whilst maintaining product performance, longevity and minimising residual product.

Valve

The valve comprises a valve body, said valve body comprising a stem and a spring means.

The valve comprises a restricted tail piece (RTP, 14) of diameter 0.50 mm to 0.55 mm, preferably 0.51 to 0.54 mm, most preferably 0.52 to 0.53 mm.

The valve comprises a vapour phase tap (VPT, 15) of diameter 0.30 mm to 0.34 mm, preferably 0.31 to 0.33 mm, most preferably 0.32 mm.

When installed in the container, the valve is preferably seated in a valve cup (16). The valve cup (16) preferably comprises an outer gasket (17), which enables connection to the can by crimping onto a can bead; and an inner gasket (18). The inner gasket controls the release product when the actuator is pressed.

Actuator

The actuator typically sits over the stem.

The actuator comprises a main spray channel and communicates with an insert.

Insert

The insert comprises an exit orifice and from 1 to 8 sub-spray channels, preferably 2 to 6 sub-spray channels, most preferably 4 sub-spray channels; wherein said channels are tangentially disposed about the exit orifice.

Suitable inserts are available from, for example, Lindal.

The insert controls the mechanical breakup.

Exit Orifice

The exit orifice is capable of being in liquid communication with the hair care formulation in the reservoir.

The exit orifice has a diameter of from 0.01 to 2 mm, most preferably 0.33 mm.

The invention will now be further described by reference to the following Examples. In the Examples, all percentages are by weight based on total weight, unless otherwise specified.

Examples

Standard LPG dry shampoo and nitrogen dry shampoo according to the invention were assessed for spray characteristics.

Assessment of the spray characteristics was conducted using a Malvern particle analyser in replicate whereby the aerosol product was sprayed for a period of 5 seconds directed through a laser beam detecting the flow and size of particles.

Assessment of the can longevity and can evacuation was conducted using a 4 dp balance and timer. The aerosol product was weighed at the beginning before any dispensing occurred followed by continuous spray of the aerosol until no further product was dispensed. Final weight of the can was measured to determine total evacuation % as compared to declared fill or actual fill contents of the product. Results depicted in the table below clearly show that the inventive example achieves comparable performance for total evacuation and particle sizing when compared to the comparative example of a Standard LPG dry shampoo. It can also be seen that the total usage time (longevity) of the invention well exceeds the comparative example.

TABLE 1

| | Standard LPG dry shampoo | Nitrogen dry shampoo |
|---|---|---|
| Can longevity | ~120 seconds | ~140 seconds* |
| Particle size D[4,3] | 22.41 microns | 34.28 microns |
| Can evacuation | >95% | >94% |

*100 seconds comparable with somewhat decreased performance in last 40 seconds

What is claimed is:

1. An aerosol hair care product comprising:
a pressurisable container at a pressure of $9 \times 10^5$ to $11 \times 10^5$ Pa, the pressurisable container comprising a container wall which encloses a reservoir;
a propellant contained within the reservoir, the propellant comprising an insoluble compressed gas and having a first weight;
a hair care formulation contained within the reservoir, the hair care formulation having a second weight and comprising starch having a third weight, the third weight being 3 to 15% of a sum of the first weight and the second weight; and
a spraying device attached to the pressurisable container, the spraying device configured to facilitate dispensing of the hair care formulation from the reservoir, the spraying device comprising:

an actuator, and
a valve comprising:
a valve body including a stem and a spring,
a restricted tail piece (RTP) having a first diameter of 0.50 millimetres to 0.55 millimetres, and
a vapour phase tap (VPT) having a second diameter of 0.30 millimetres to 0.34 millimetres.

2. The aerosol hair care product of claim 1, wherein the insoluble compressed gas is nitrogen.

3. The aerosol hair care product of claim 1, wherein the pressure is $10 \times 10^5$ to $11 \times 10^5$ Pa.

4. The aerosol hair care product of claim 1, wherein the first diameter is 0.51 millimetres and the second diameter is 0.32 millimetres.

5. The aerosol hair care product of claim 1, wherein the propellant comprises a liquefied gas mixed with the insoluble compressed gas.

6. The aerosol hair care product of claim 5, wherein:
the liquefied gas has a fourth weight; and
the fourth weight is 3% to 16% of the second weight.

7. The aerosol hair care produce of claim 5, wherein the liquefied gas comprises a liquefied petroleum gas or a hydrofluorocarbon.

8. The aerosol hair care product of claim 1, wherein the second weight is 85% to 95% of the sum.

9. The aerosol hair care product of claim 8, wherein the second weight is at least 89% of the sum.

10. The aerosol hair care product of claim 8, wherein the second weight is not more than 90% of the sum.

11. The aerosol hair care product of claim 10, wherein the second weight is at least 89% of the sum.

12. The aerosol hair care product of claim 1, wherein the pressurisable container has a volume of 300 millilitres.

13. The aerosol hair care product of claim 1, wherein the starch comprises corn starch, tapioca starch, rice starch, modified corn starch, modified tapioca starch, or aluminium starch octenyl succinate.

14. The aerosol hair care product of claim 1, wherein the hair care formulation comprises isopropyl myristate.

15. The aerosol hair care product of claim 14, wherein:
the isopropyl myristate has a fourth weight; and
the fourth weight is 0.5% to 4% of the sum.

16. The aerosol hair care product of claim 1, wherein the hair care formulation comprises an alcohol.

17. The aerosol hair care product of claim 16, wherein:
the alcohol has a fourth weight; and
the fourth weight is 50% to 90% of the sum.

18. The aerosol hair care product of claim 17, wherein the alcohol comprises ethanol, isopropyl alcohol, or butanol.

19. The aerosol hair care product of claim 16, wherein the alcohol comprises ethanol, isopropyl alcohol, or butanol.

20. The aerosol hair care product of claim 1, further comprising a valve cup having an outer gasket;
wherein the valve is seated in the valve cup;
wherein the container wall comprises a bead; and
wherein the outer gasket is crimped onto the bead.

* * * * *